United States Patent [19]

Couchman

[11] 4,295,377
[45] Oct. 20, 1981

[54] FASTENER INCORPORATING REMOVABLE ULTRASONIC TRANSDUCER

[75] Inventor: James C. Couchman, Fort Worth, Tex.

[73] Assignee: General Dynamics Corporation, Fort Worth, Tex.

[21] Appl. No.: 57,057

[22] Filed: Jul. 12, 1979

[51] Int. Cl.³ .................. F16B 31/02; G01N 29/00
[52] U.S. Cl. .................................................. 73/761
[58] Field of Search ................ 73/761, 629, 597; 116/DIG. 34; 310/336

[56] References Cited

U.S. PATENT DOCUMENTS

| Re. 30,183 | 1/1980 | Popenoe | 73/761 |
| 3,201,977 | 8/1965 | Kutsay | 73/761 |
| 4,014,208 | 3/1977 | Moore et al. | 73/761 |
| 4,127,788 | 11/1978 | Daugherty | 73/761 |

FOREIGN PATENT DOCUMENTS 52-73781 6/1977 Japan ..................... 73/761

*Primary Examiner*—Anthony V. Ciarlante
*Attorney, Agent, or Firm*—Arthur F. Zobal

[57] ABSTRACT

A threaded fastener incorporating a removable ultrasonic transducer for obtaining preload measurements as well as other measurements for quality control inspection or for monitoring purposes. The transducer may be removed for repair or replacement purposes.

21 Claims, 8 Drawing Figures

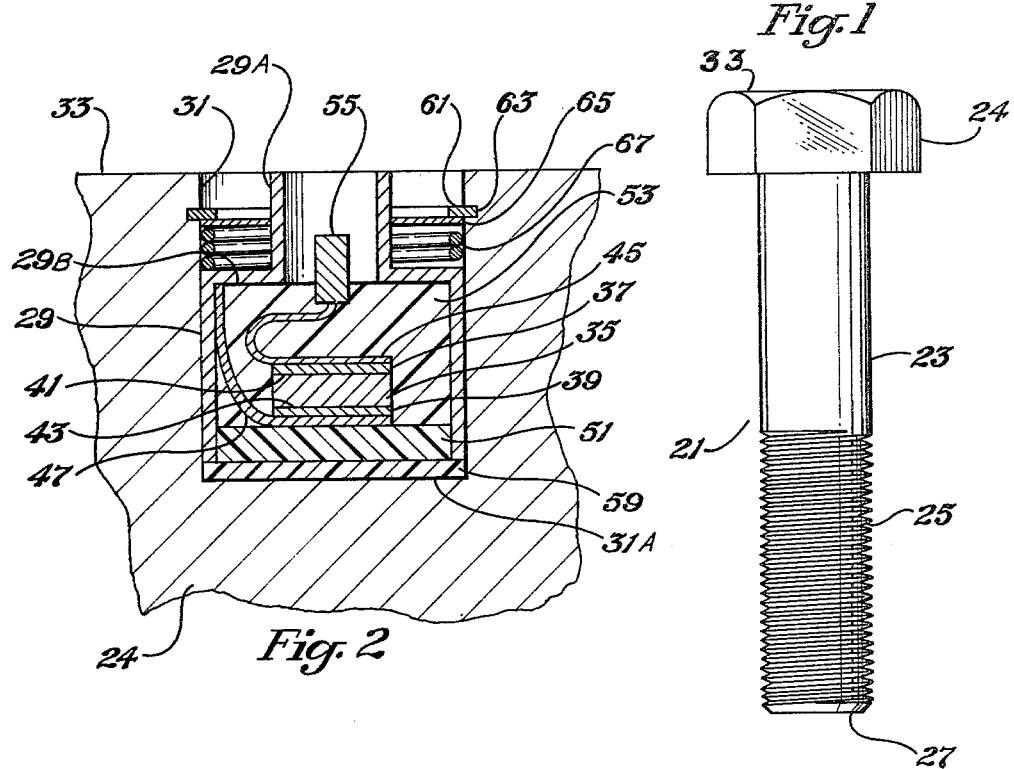
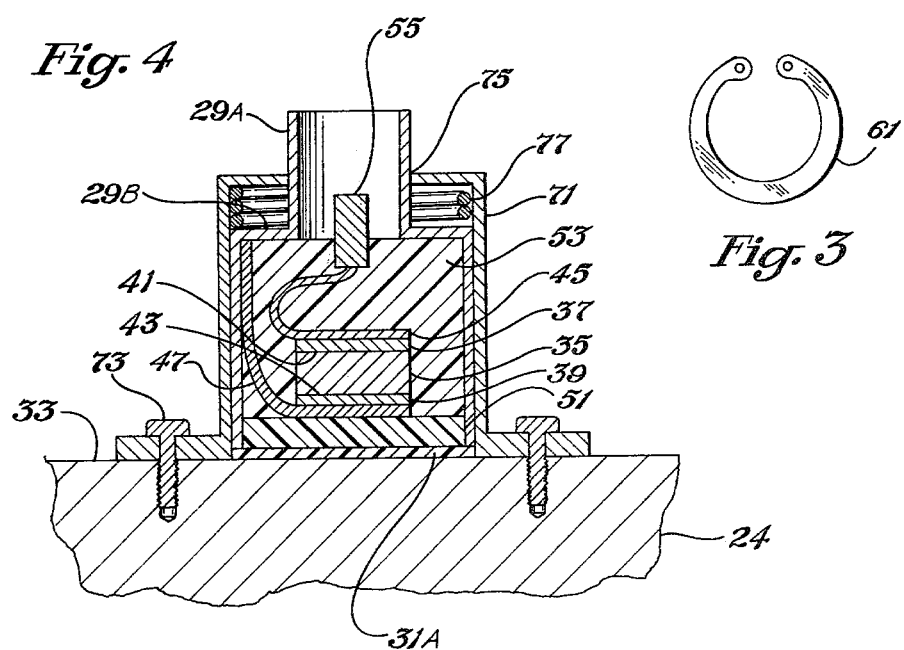

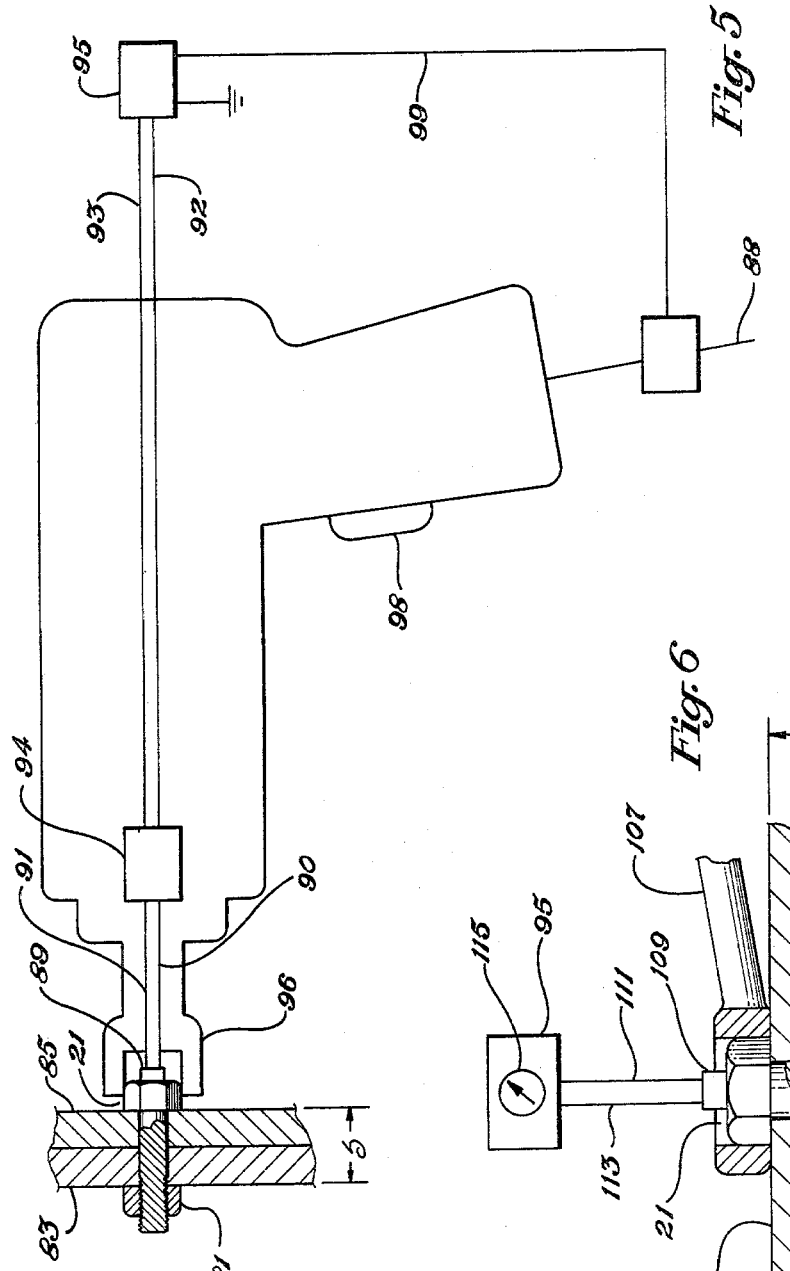
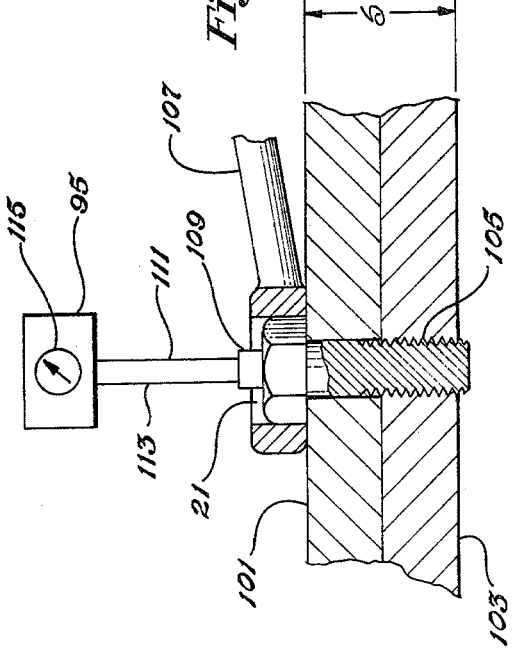

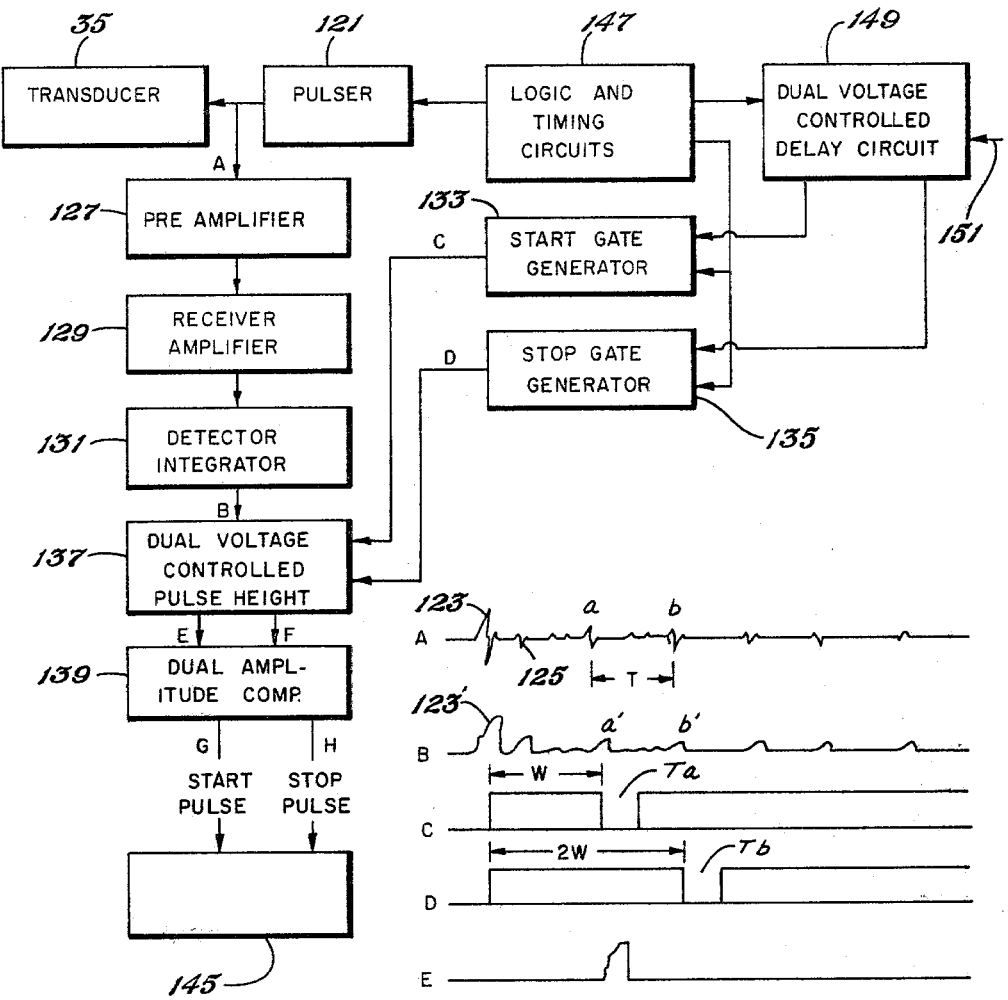

FASTENER INCORPORATING REMOVABLE ULTRASONIC TRANSDUCER

The Government has rights in this invention pursuant to Contract No. F33615-76-C-5251 awarded by the Department of the Air Force.

FIELD OF THE INVENTION

The present invention relates to the measurement of preload on a threaded fastener and more particularly to a threaded fastener incorporating a removable ultrasonic transducer for allowing accurate measurements of preload to be obtained as well as other measurements for quality control inspection or for monitoring purposes.

DESCRIPTION OF THE PRIOR ART

In aircraft, space vehicles, and other types of vehicles, it is important that bolt fasteners be properly preloaded (tightened) to prevent structural failure. This is particularly true with respect to fasteners employed in critical load bearing structures. It has been found that the conventional hand operated torque wrench may result in errors of 30% or higher in pretensioning a bolt to the desired preload. Thus means is desired that will accurately measure the true preload on a bolt.

Pulse-echo and resonant frequency techniques have been developed to obtain more accurate measurements of the preload obtained on a bolt when torqued. Pulse-echo techniques are disclosed in U.S. Pat. Nos. 3,759,090 and 3,969,810 and a resonant frequency technique is discussed by Heyman, J. S., "Ultrasonic Bolt Stress Monitor" Industrial Research, Oct. 1976; Lutz-Nagey, R. C., "Torque Verification from Eyeball to Accuracy," Automation, October 1976; and Langley Research Center, "ROUS Bolt Tensioning Monitor," NASA Tech Brief, Summer 1976. The pulse-echo technique is preferred over the resonant frequency technique since it is more accurate and allows measurements to be obtained faster.

In the prior pulse-echo and resonant frequency techniques employed in making preload measurements, an ultrasonic transducer is temporarily clamped to the head of the bolt with an acoustic coupling oil or other suitable coupling medium located between the transducer and the bolt. U.S. Pat. No. 3,759,090 discloses a manual clamping technique while U.S. Pat. No. 3,969,810 discloses an automatic torque wrench which carries the transducer in the wrench head and allows measurements to be obtained while torquing.

In these prior techniques, the transducer is clamped to the fastener only during preloading measurements and can not be used for making subsequent measurements on the fastener or for monitoring purposes. Moreover, an automatic torque wrench which carries the transducer in the wrench head has disadvantages in that slippage occurs between the transducer and the bolt head during torquing. In the pulse-echo technique, this slippage introduces a time error which even though only a few nanoseconds, is enough to prevent accurate time measurements.

SUMMARY OF THE INVENTION

It is an object of the present invention to provide a threaded fastener which carries a removable (or replaceable) transducer; i.e., in a semi-permanent manner, which may be employed to readily obtain accurate preload measurements without slippage as well as subsequent measurements to detect for flaws or cracks or which may be employed subsequently for monitoring purposes.

It is a further object of the present invention to provide a threaded fastener carrying an attaching means for attaching an acoustic transducer to the fastener whereby the transducer also will be carried by the fastener. The attaching means allows the transducer to be removed for repair or replacement purposes.

BRIEF DESCRIPTION OF DRAWINGS

FIG. 1 illustrates a conventional threaded fastener.

FIG. 2 is an enlarged cross section of the head of a fastener similar to FIG. 1 illustrating one embodiment for removably attaching a transducer to the head.

FIG. 3 illustrates a snap ring which may be used in the embodiment of FIG. 2.

FIG. 4 illustrates another embodiment for removably attaching a transducer to the top of a fastener.

FIG. 5 illustrates an automatic torque wrench torquing a fastener of the present invention in place while preload measurements are obtained.

FIG. 6 illustrates a hand wrench torquing a fastener of the present invention in place while preload measurements are obtained.

FIG. 7 is an electrical block diagram of a system of circuitry for obtaining preload or other measurements.

FIG. 8 are timing diagrams useful in understanding the system of FIG. 7.

DESCRIPTION OF THE PREFERRED EMBODIMENTS

Referring now to FIG. 1 of the drawings, reference numeral 21 identifies a conventional metallic fastener or bolt used in aircraft, space vehicles, and in other types of vehicles for securing structural members together. It may be formed of steel, titanium, aluminum, or other metals or alloys. The fastener comprises a shank 23 having a head 24 formed at one end and threads 25 formed at the other end 27 to which a nut may be threaded.

Referring to FIG. 2, a cylindrical opening 31 or recess means is formed in the top center of the head 24 from its flat surface 33 downward toward the shank. Removably secured in the opening 31 is a cylindrical metallic member 29 carrying an ultrasonic transducer element 35 formed of a piezoelectric material such as Pb Zr Ti. The transducer is disc shaped and has thin layers of electrically conducting metal 37 and 39 secured to opposite ends or surfaces 41 and 43 respectively. Layers 37 and 39 may be secured to ends 41 and 43 by conventional techniques. Secured to layers 37 and 39 are electrodes 45 and 47 respectively which may be tin strips secured in a conventional manner. Secured within the lower end of member 29 is a layer of material 51 (which may be suitable plastic) having good acoustic coupling properties. The transducer element 35 is located such that its electrode 47 rests against layer 51 and is embedded in member 29 by a potting material 53 which has good acoustic damping properties. Electrode 45 is in electrical contact with a metallic pin terminal 55 held in place by the potting material 53. Electrode 47 extends upward and is electrically connected to member 29 allowing its neck 29A to be employed as a terminal. The potting material damps out ultra sound vibrations traveling upward toward terminal 55. A layer of oil, grease or other suitable media 59 is located between layer 51 and the lower surface 31A of opening 31 for purposes of acoustic coupling.

Member 29 and hence transducer element 35 is held in the opening by a C-shaped snap ring removably located in slot 63. Located below the snap ring 61 is a washer 65 which acts a dust cover. A coil spring 67 engages the lower surface of the washer 65 and the outer portion of the shoulder 29B of member 29 to urge member 29 and its layer 51 tightly in the opening against the coupling medium 59. In order to remove member 29 and hence the transducer for replacement or other purposes, one merely has to remove the snap ring 61 and lift the member 29 out of the opening 31.

Since the transducer is carried by the fastener, preload measurements may be readily made while torquing with an automatic torque wrench and a permanent record may be obtained of each preload. No slippage will occur between the transducer and the bolt head. In addition, at a later date, the transducer may be used to recheck preload or to detect for flaws or cracks in the bolt fastener or to monitor for acoustic emissions resulting from bolt or adjacent structural failure. If the transducer deteriorates or becomes faulty, it can be readily replaced or repaired.

In using the embodiment of FIG. 2 for measurement or monitoring purposes, circuitry will be electrically coupled to terminal 55 and terminal 29A will act as a return terminal.

It is to be understood that member 29 and its transducer element 35 may be removably secured with snap ring 61 in an opening (not shown) formed in the bottom end 27 of the bolt 21 instead in opening 31 of the bolt head. The transducer may be used in the same manner as when removably secured in the opening 31 of the head 24. The embodiment wherein the transducer element 35 is removably secured in an opening formed in end 27 of the fastener will not be employed when the fastener is torqued into a threaded opening in a structural member.

Referring now to FIG. 4, the member 29 with its transducer element 35 is shown removably secured to the top surface 33 of the fastener 24 by way of a cap 71 and bolts 73. As shown, cap 71 fits around the member 29 with its neck 29A extending through an upper opening 75 formed in the cap. A coil spring 77 engages the upper inner surface of cap 71 and the outer edge of shoulder 29B for urging the member 29 and its layer 51 tightly against the coupling medium 59. In order to remove member 29 and hence transducer element 35 for replacement or other purposes, one merely has to remove bolts 73 and the cap 71. In the embodiment of FIG. 4, since the transducer is carried by the fastener, preload measurements can be readily made while torquing with an automatic or manual torque wrench and a permanent record may be obtained of each preload. No slippage will occur between the transducer and the bolt head. In addition, at a later date, the transducer may be used to recheck preload or to detect for flaws or cracks in the bolt fastener or to monitor for acoustic emissions resulting from bolt or adjacent structural failure. If the transducer deteriorates or becomes faulty, it can be readily repaired or replaced.

It is to be understood that the cap 71 may be employed to removably secure member 29 and its transducer element to the threaded end 27 of the fastener instead of to the top of the bolt head 24.

Pulse-echo time measurements for preload may be made with the embodiments of FIGS. 2-4 whether the fastener is torqued with an automatic wrench or with a manual wrench. In FIG. 5, the bolt 21 and a nut 81 are employed to fasten together two plates 83 and 85. The bolt 21 employs the embodiments of FIG. 2. A power driven wrench 87 is shown in outline form for torquing the fastener and the nut 81 together. The means for holding the nut 81 is not shown. The wrench 87 has a socket 96 pneumatically driven or electrically driven. Reference numeral 88 identifies pneumatic or electrical lines for applying power to the wrench. An electrical socket 89 is fitted to terminals 55 and 29A for connecting the terminals to leads 90 and 91 respectively. Leads 90 and 91 are coupled to leads 92 and 93 respectively by way of means 94 which allows leads 90 and 91 to rotate relative to leads 92 and 93. Leads 92 and 93 are electrically connected to a pulse-echo measuring system 95. When good pulse-echo signals are being detected within the desired electronic time window or windows, a light will turn on signaling to the operator to actuate the trigger 98 to apply power to the wrench to tighten the bolt. When the desired preload or stress is achieved, the system 95 issues a command by way of line 99 to cut off power to the wrench. If too much stress is measured, the system 95 will issue a command to the wrench (by means not shown) to back off until the desired stress is achieved.

When the fastener has been tightened to the desired preload, the socket 96 of the wrench 87 is removed and member 29 with its transducer element 35 are left in place attached to the fastener. The transducer may be used at a later time to recheck preload or to detect for flaws or cracks or to monitor for acoustic emissions resulting from structural failure.

In FIG. 6, the bolt 21 is employed to fasten together plates 101 and 103, the latter of which has threads 105 formed within its aperture. The bolt 21 employs the embodiment of FIG. 2. A manual wrench 107 is shown for torquing bolt 21 into threads 105 for fastening together plates 101 and 103. An electrical socket 109 is fitted to terminals 55 and 29A for connecting these terminals respectively to leads 111 and 113 which extend to the pulse-echo measuring system 95. A meter 115 is employed to measure torque by the pulse-echo technique while the bolt 21 is being torqued by wrench 107. When the desired preload is achieved, the wrench 107 is removed and member 29 with its transducer element 35 is left in place attached to the bolt. The transducer may be used at a latter time to recheck preload or to detect for flaws or cracks in the bolt or to monitor for acoustic emissions resulting from structural failure.

Referring now to FIGS. 7 and 8, there will be described a preferred pulse-echo technique for measuring preload stress. For these measurements, the transducer will have a frequency of from 0.5 MHZ to 200 MHZ. A pulser 121 is employed for pulsing the transducer at a repetition rate of 100-2000 pulses per second. Each time the transducer is pulsed, an acoustics signal will travel to the end of the bolt and back a number of times until the signal is attenuated or damped out. Preferably the first and second back echos (signals reflected from the other end of the fastener) are measured and the time difference between the signals is determined. In FIG. 8A, 123 represents an acoustic pulse generated by the transducer element 35 when it is pulsed. The first back echo is identified at a and the second back echo is identified at b. Signal 125 is an echo signal due to reflections from interfaces between coupling layers. For example, in FIG. 2 such a signal will be produced from interfaces between layers 51, 59, and surface 31A. The signals to the right of signal b are third, fourth, and fifth back echo signals. The times of the first and second back echo signals a and b are measured and the difference obtained to subtract out the travel times in any acoustic medium employed. The time difference is indicated to be equal to T. The time T is measured prior to preload to obtain $T_0$ and during torquing to obtain $T_t$. The difference between $T_t$ and $T_0$ is found to obtain $\Delta T$ as follows.

$$\Delta T = T_t - T_0 \qquad (1)$$

It can be shown that stress S on the bolt is equal to $$S = \frac{M}{\delta + \alpha D} \Delta T \qquad (2)$$

wherein:
M is a material constant,
$\delta$ is the grip length (See FIGS. 5 and 6),
D is the diameter of the shank of the fastener, and
$\alpha$ is an empirically determined parameter which corrects for stress distribution in fasteners. This has been experimentally determined for typical high strength steel fasteners to be about 0.6.

In obtaining measurements of the first and second back echo signals a and b, two electronic time windows are set following the pulse 123 where signals a and b are expected to occur. The position of these windows depend upon the length of the fastener and the velocity of sound in the material of the fastener. Thus, knowing the properties of the material of the fastener, its length and diameter, and the grip length, one can measure $\Delta T$ to measure stress to obtain an accurate measure of bolt preload.

Referring again to FIGS. 7 and 8, the output of transducer at A is shown in FIG. 8A. This output is applied to a pre-amplifier 127, a receiver amplifier 129, and a detector integrator 131 whose output is shown in FIG. 8B. Detector integrator 131 is a full wave rectifier and integrator. Start and stop gate generators 133 and 135 produce gating signals at times $T_a$ and $T_b$ when the first and second back echo signals are expected respectively. Their outputs are shown in FIGS. 8C and 8D respectively. Dual voltage controlled pulse height circuit 137 converts the first and second back echo signals passed to it at times $T_a$ and $T_b$ to the same heights to correct for attenuation in the fastener. The output of circuit 137 at E and F are shown in FIGS. 8E and 8F respectively. These output signals are applied to dual amplitude comparitor circuit 139 where they are converted to square wave signals shown at 141 and 143 in FIGS. 8G and 8H respectively. These signals then are applied to a time interval counter 145 which counts the time between the leading edges of square wave signals 141 and 143 to obtain T. The leading edge of square wave signal 141 turns on the counter and the leading edge of square wave signal 143 turns it off. As stated above, $T_0$ is measured prior to preload and $T_t$ is measured during torquing to obtain $\Delta T$ and hence stress. Circuitry will be provided for averaging $\Delta T$ over a plurality of cycles and for automatically solving equation 2.

In the system of FIG. 7, pulser 121 is a free-running pulser which produces a pulse at a repetition rate of 100–2000 pulses per second. The logic in timing circuits 147 senses each pulse and sends a signal to start the two gate generators 133 and 135 during each cycle. It also sends a signal to the dual voltage controlled delay circuit 149 which starts two timers. The timers may be charging capacitors, one of which charges at a rate twice as fast as the other. A voltage representative of the two way travel time between the transducer and the other end of the fastener is applied to circuit 149 at 151 and compared with the voltages of the timers. When the voltages of the timers reach the level of the input voltage at 151, the timers are cut off and their associated gate generators are caused to generate the gating signals $T_a$ and $T_b$.

In order to detect for flaws or cracks in the fastener, one merely needs to look at the output of the detector integrator 131 on a oscilloscope or readout. The absence of one or both of the signals a' and b' or changes in their heights indicates possible flaws in the fastener. The appearance of another signal between 123' and a' indicates that the fastener has a crack in it.

One may use the embodiments of FIGS. 2–4 to look for acoustic emissions or for other diagnostic purposes while the vehicle is in operation or flight and which may result from bolt or adjacent structural failure. In this embodiment, the pulser 121 will not be employed. The output of the transducer will be coupled to circuits 127, 129, and 131 and the output of circuit 131 will be monitored. FIG. 6 illustrates one way in which acoustic emissions, which may occur while the vehicle is in operation or in flight due to bolt or adjacent structural failure, may be monitored. The embodiment of FIG. 2 is shown in this figure. The system 93 will have a suitable readout for monitoring for acoustic emissions from the bolt or from the adjacent structure.

The system of FIG. 6 also may be used to allow one to monitor for cracks or flaws in critical fasteners periodically or continuously during operation or while in flight. In this embodiment, the pulser 121 will be employed and the output of the detector integrator 131 will be monitored as described previously.

Since the transducer is carried by the fastener, improved quality control can also be obtained. In this respect, the fastener can be tested prior to use to determine if good echo signals are received or if other noise signals appear as described above. If flaws or cracks exist, the fastener may be discarded.

As now can be understood, accurate preload measurements can be readily obtained using the fastener of the present invention. There will be no slippage between the transducer and the fastener during torquing and in addition, assurance will be had that optimum echo signals will be obtainable. Moreover, subsequent measurements can be readily made with the same transducer to recheck for preload and to measure and monitor for cracks and flaws and for acoustic emissions. In the event that the transducer deteriorates or becomes faulty at a later date it may be readily repaired or replaced.

Although pulse-echo techniques were described in making measurements employing the fasteners of the embodiments of FIGS. 2–4, it is to be understood that the embodiments of FIGS. 2–4 may be used in obtaining preload measurements employing resonant frequency techniques.

I claim:
1. A fastener, comprising:
   a shank having a head at one end and threads formed at the other end,
   an acoustic transducer located in a container means and affixed therein such that said transducer and said container means are an integral unit, and attaching means for removably attaching said container means to one end of said fastener with said acoustic transducer being acoustically coupled to said fastener to allow pulse-echo measurements to be obtained while said fastener is torqued in place with a wrench means, said attaching means being separate from the wrench means whereby when the wrench means is removed from said fastener, said container means remains attached to said fastener, the entire portion of said fastener between said container means and the end of said fastener opposite said container means being of solid metal throughout.

2. The fastener of claim 1, wherein:
said transducer is affixed in said container means with potting material.

3. The fastener of claim 11, wherein:
said container means is located in a shallow opening formed in said one end of said fastener and removably attached therein.

4. The fastener of claim 3, wherein:
said attaching means comprises removable holding means located in said opening.

5. The fastener of claim 4, comprising:
spring biasing means located in said opening and seated against said removable holding means and said container means.

6. The fastener of claim 3, wherein:
said shallow opening is formed in said head only of said fastener.

7. The fastener of claim 1, wherein:
said container means is removably attached to the exterior surface of said one end of said fastener.

8. The fastener of claim 7, wherein:
said attaching means comprises cap means located around said container means and removably secured to said exterior surface of said one end of said fastener.

9. The fastener of claim 8, comprising:
spring biasing means located in said cap means and seated against said cap means and said container means.

10. The fastener of claim 7, wherein:
said attaching means removably attaches said container means to the exterior surface of said head of said fastener.

11. The fastener of claim 1, wherein:
said attaching means removably attaches said container means to said head of said fastener.

12. A fastener comprising:
a shank having a head at one end and threads formed at the other end,
a shallow opening formed in one end of said fastener,
said opening having a depth less than the length of said head as measured along the longitudinal axis of said fastener,
an acoustic transducer located in said opening,
attaching means for removably attaching said transducer in said opening with said transducer acoustically coupled to said fastener,
said fastener being formed of metal with the portion of said fastener between said opening and the end of said fastener opposite said opening being of solid metal throughout.

13. The fastener of claim 12, wherein:
said transducer is located in said opening such that it may be used for pulse-echo measurements wherein when said transducer is pulsed, a transducer signal is generated which travels from said transducer through said fastener to said end of said fastener opposite said opening and back to said transducer at least once, the distance between said transducer and said end of said fastener opposite said opening being equal to a major portion of the length of said fastener such that when said signal is generated it will travel through the entire gripping length of said fastener, including the portion of said shank next to said head, when traveling between said transducer and said end of said fastener opposite said opening.

14. The fastener of claims 12 or 13 wherein:
said opening is formed in said head only of said fastener.

15. The fastener of claim 12 or 13, wherein:
said opening is formed in said one end only of said fastener.

16. A fastener comprising:
a shank having a head at one end and threads formed at the other end,
a shallow opening formed in one end of said fastener,
an acoustic transducer located in said opening,
attaching means for removably attaching said transducer in said opening with said transducer acoustically coupled to said fastener such that it may be used for pulse-echo measurements wherein when said transducer is pulsed, a transducer signal is generated which travels from said transducer through said fastener to the end of said fastener opposite said transducer and back to said transducer at least once, the distance between said transducer and said end of said fastener opposite said opening being equal to a major portion of the length of said fastener such that when said signal is generated it will travel through the entire gripping length of said fastener, including the portion of said shank next to said head, when traveling between said transducer and said end of said fastener opposite said opening, the entire portion of said fastener between said opening and said end of said fastener opposite said opening being of solid metal throughout.

17. The fastener of claim 16, wherein:
said opening is formed in said head only of said fastener.

18. The fastener of claim 16, wherein:
said opening is formed in said one end only of said fastener.

19. The fastener of claim 12, 13, 16, 17, or 18 wherein:
said attaching means comprises removable holding means located in said opening.

20. The fastener of claim 12, 13, 16, 17 or 18 wherein said attaching means comprises:
removable holding means located in said opening, and
spring biasing means located in said opening and seated against said removable holding means for tightly holding said transducer in said opening in an acoustically coupled relationship with said fastener.

21. The fastener of claim 12, 13, 16, 17, or 18 wherein:
said acoustic transducer is acoustically coupled to said fastener to allow pulse-echo measurements to be obtained while said fastener is torqued in place with a wrench means,
said attaching means being separate from the wrench means whereby when the wrench means is removed from said fastener, said transducer remains attached to said fastener.

* * * * *